United States Patent [19]

Robertson

[11] Patent Number: 4,873,707
[45] Date of Patent: Oct. 10, 1989

[54] X-RAY TOMOGRAPHY PHANTOMS, METHOD AND SYSTEM

[75] Inventor: Douglas D. Robertson, Waltham, Mass.

[73] Assignee: Brigham & Women's Hospital, Boston, Mass.

[21] Appl. No.: 95,191

[22] Filed: Sep. 11, 1987

[51] Int. Cl.$^4$ .............................................. A61B 6/00
[52] U.S. Cl. ..................................... 378/18; 378/207; 128/653; 324/308
[58] Field of Search ............... 378/18, 156; 250/505.1; 128/653, 660.01, 660.07; 324/308

[56] References Cited

U.S. PATENT DOCUMENTS

| | | | |
|---|---|---|---|
| 3,010,223 | 11/1961 | Alderson | 378/18 |
| 3,881,110 | 4/1975 | Hounsfield et al. | 378/18 |
| 4,126,789 | 11/1978 | Vogl et al. | 378/18 |
| 4,296,329 | 10/1981 | Mirabella | 250/491.1 |
| 4,331,869 | 5/1982 | Rollo | 252/252.1 |
| 4,333,010 | 6/1982 | Miller | 250/505.1 |
| 4,344,183 | 8/1982 | Jacobson | 378/207 |
| 4,352,020 | 9/1982 | Horiba et al. | 378/18 |
| 4,436,684 | 3/1984 | White | 378/18 |
| 4,472,829 | 9/1984 | Riederer et al. | 378/207 |
| 4,646,334 | 2/1987 | Zerhonni | 378/18 |
| 4,649,561 | 3/1987 | Arnold | 378/207 |
| 4,655,716 | 4/1987 | Hoevel | 434/267 |
| 4,663,772 | 5/1987 | Mattson et al. | 378/18 |

OTHER PUBLICATIONS

Seitz et al., "Fast Contour Detection Algorithm for High Precision Quantitative CT", IEEE Transactions on Medical Imaging, vol. MI-2, No. 3, Sep. 1983, pp. 136-141.

Coleman et al., "A Beam-Hardening Correction Using Dual-Energy Computed Tomography", Phys. Med. Biol., vol. 30, No. 11, 1985, pp. 1251-1256.

Robertson et al., "Quantitative Bone Measurements Using X-ray Computed Tomography with Second-Order Correction", Medical Physics, vol. 13, No. 4, Jul.-Aug. 1986, pp. 474-479.

Granholm et al., "Computer Design of Custom Femoral Stem Prosthesis", IEEE CG and A, Feb. 1987, pp. 26-35.

Primary Examiner—Craig E. Church
Assistant Examiner—John C. Freeman
Attorney, Agent, or Firm—Saidman, Sterne, Kessler & Goldstein

[57] ABSTRACT

A computed tomography system which includes both a high-energy imaging apparatus (such as an X-ray computed tomography device) and also one or more phantoms whose solid characteristics generally correspond to the density and shape (preferably including external and internal contours) of the existing object to be imaged. The phantom is used for differential error-correction techniques, which permit very accurate imagining of the contours of bones in vivo. The accurate images thus derived permit fabrication of orthopedic prostheses which have an extremely accurate fit to existing bone structure.

14 Claims, 2 Drawing Sheets

X-RAY TOMOGRAPHY PHANTOMS, METHOD AND SYSTEM

BACKGROUND OF THE INVENTION

The present invention relates to phantoms for use in the measurement of difficult-to-access structures (especially physiological structures within a living organism) using a high-energy scanning apparatus. The invention also relates to a process and system for measuring these structures.

High-energy imaging methods have long been used for measurement of anatomical structures. Originally, this was done simply by putting a subject between an X-ray source and a photosensitive emulsion.

In recent years, X-ray computed tomography devices have provided a greatly improved imaging capability. Such machines collect X-ray absorption values along various axes in a plane (e.g. by moving the X-ray sensor, and moving the effective position of the X-ray source, around a subject). This set of absorption values provides sufficient data to define a two-dimensional cross-sectional image. By repeatedly advancing the subject and rescanning, multiple two-dimensional images are produced. These two-dimensional images can be combined with the aid of a computer to form a three-dimensional image of the scanned object. (The contour of the three-dimensional image will be somewhat inexact, since the two-dimensional images are separated by "gaps" corresponding to finite increments between successive scans.)

The data obtained from the scanning apparatus is used to construct the two- and three-dimensional images. This technique has been of tremendous utility in diagnostic procedures. However, the scanning machines and methods have not yet achieved their full potential benefits in applications where it is necessary to do precise imaging in the neighborhood of high-density objects. Some of the inherent limitations of these otherwise-useful measurement methods are unacceptable in applications such as precise bone imaging. These errors result from scatter, beam hardening, and partial volume effects.

"Scatter" refers to the unwanted misdirection of some of the X-rays when passing through an object being scanned, causing a somewhat distorted image when some of these misdirected X-rays are sensed by an X-ray sensing device.

"Beam hardening" is a general problem in high-energy imaging. The absorption of different materials varies with wavelength, but the X-ray detectors normally used are not spectrally sensitive. (The X-ray sources normally used for imaging are not monochromatic, and will in fact include an energy spread over a quite significant range of energies.) That is, when bone (or other dense material) is exposed to X-rays, a higher fraction of the lower-energy X-ray photons will be absorbed than of the higher-energy X-ray photons. The reconstruction algorithm may therefore underestimate the density of the region imaged, since the transmitted high-energy photons will mask the fact that a very high percentage of the lower-energy photons have been absorbed or scattered. Thus, failure to correct for beam hardening effects may cause incorrect estimation of material densities. This is particularly a problem when imaging high-density materials, such as bone.

Most computed tomography systems include algorithmic correction for the beam hardening effects of soft tissue. However, the beam hardening effects of bone are not easy to correct for. Conventional methods have not successfully corrected for this, and therefore it has not been possible to get accurate dimensional measurements of bone structures in situ.

"Partial volume effects" result from the fact that the beam will have a finite width or aperture (for example, 40 to 80 millimeters), and therefore the absorption measurements for volumes between the beam source and the image plane will actually be averaged measurements over a certain cross-sectional area.

There are other difficulties in imaging neighborhoods of high-density materials. One difficulty is that the image reconstruction algorithms typically will produce some "smear," due to the fact that the algorithms used to deconvolve the sensed values are imperfect. Thus, for example, an artificially high density may be estimated for the volume within a bone ring.

Another effect is that incorrectly low densities may be estimated for the volume between two bones which are in close proximity to each other (these errors are known as "interosseous lucencies").

A further problem resulting from interosseous lucencies is that estimation of the boundaries between cortical bone (the outermost layer of hard bone) and cancellous bone (the layer of lower density bone which (e.g. in a femur) separates the cortical bone from the marrow) may be very difficult to do correctly. Similarly, estimation of the boundary between cancellous bone and bone marrow may be difficult to do correctly, and estimation of the boundary between cortical bone and surrounding soft tissue may also be very difficult to do correctly. As will be discussed below, precise measurement of these contours (particularly the cancellous/marrow boundary) is extremely useful in certain diagnostic and surgical procedures.

In the past, computed tomography has been used in conjunction with phantoms in order to adjust X-ray computed tomography scanning equipment for variations in attenuation (density) readings. Factors creating a need for this adjustment include aging X-ray tubes and the general sophistication of the equipment used.

Phantoms such as the one described in Zerhouni (U.S. Pat. No. 4,646,334) have been used to calibrate X-ray computed tomography devices using materials of known density. In particular, this patent relates to a phantom containing a material having X-ray attenuation properties similar to a lung nodule. Using this phantom, a computed tomography scanner is calibrated to more selectively detect malignant lung nodules (which have been found to have attenuation properties differing from benign lung nodules). Surrounding the nodule portion of the phantom is other material with shape and attenuation properties similar to the bone and tissue found in and around the lung of a human or non-human animal. This surrounding tissue serves as a means by which the phantom can more closely resemble an animal tissue structure for attenuation calibration purposes. Correction for measurement and sizing errors are not seen to be addressed by this teaching.

Fitting prosthetic hip-stems is an area of application where more accurate measurement capability would be very useful, and where imaging difficulties caused by the proximity of bone are important. The prosthetic hip-stem must be fitted to the inner cortical canal of the femur into which the hip-stem is to be inserted. Accurate measurement is particularly needed it is not desirable to cement the hip-stem to the femur canal.

For example, younger patients, more active patients, and overweight patients will predictably suffer some degradation of artificial hip-stems over time, so that repeated prosthesis operations may be necessary. Similarly, patients who have previously had an infected prothesis will be preferred candidates for non-cemented implants, since reduction of the amount of foreign material lessens the chance of resulting infection.

Thus, it is desirable to provide methods for hip-stem prosthesis which do not require that the hip-stem be cemented, in order to permit removal and replacement of the hip-stems if that should later become necessary. However, non-cemented implants require a much closer fit to the femur canal than would be required for a cemented implant. It is therefore desirable to have an accurate measurement of the femur canal before the surgical procedure is started, to minimize fitting procedures during surgery.

In the past, quantitative computed tomography measurement techniques have been used to generate three-dimensional representative data of the femur canal so that custom hip-stems could be produced. However, the hip-stems manufactured using these techniques did not provide optimal fit, since only a few of the many femur canal curvatures and dimensions were used in the hip-stem design process. Specifically, the fit provided was not adequate for non-cemented prosthesis.

In addition, in the prior methods for hip-stem prosthesis, the actual hip-stem design was done by hand. However, U.S. Pat. No. 4,436,684 to White (which is hereby incorporated by reference) suggests a non-invasive method of forming prostheses of skeletal structures internal to a body for use in reconstructive surgery. This method uses data derived from imaging to control a sculpting tool to form an appropriate prosthesis. It would be desirable to be able to use equally rapid methods to form hip-stem prostheses, but the measurement capabilities presently available have not provided sufficient accuracy to permit this.

Thus, it is an object of the present invention to provide a means for correcting errors produced from a high-energy scanning device such as an X-ray computed tomography scanner. Since such errors are significant, a means for eradicating them would be a welcome contribution to the medical/scientific community.

SUMMARY OF THE INVENTION

The above problems, and other problems, are resolved by the present invention, which provides a device, a method, and a system for the accurate measurement of an existing object within a difficult-to-access region.

One of the innovative teachings disclosed herein is a phantom which generally corresponds to the shape and contour structure of the internal and external surfaces of the existing object or portion thereof. The phantom is used in conjunction with a high-energy scanning apparatus to permit differential error-correction techniques which assist in the correction of the errors previously discussed.

The phantom of the present invention preferably consists of a material or materials having bulk (three-dimensional) high-energy absorption properties substantially similar to that of the existing object.

Another of the novel teachings herein provides that the phantom can optionally be made hollow, with a liquid-tight sealable cavity. This allows the hollow phantom to be filled with a liquid or foamed substance which has high-energy absorption properties similar to those of the core of the existing object.

Where the existing object includes different layers (and/or a core) of substances which have different respective high-energy absorption properties, the phantom preferably contains layers and/or a core (solid or liquid) of materials which have substantially similar high-energy absorption properties to that of the existing object. For example, the embodiments where a hollow phantom is used advantageously permit the phantom to be filled with any of a number of different materials, so as to optimally simulate the high-energy absorption properties of a wide variety of different existing objects.

A further point of invention is that one phantom can be constructed for use with a class of existing objects having a range of sizes (and, optionally, of shapes). A single phantom with an appropriate range of inner and outer sizes will include at least one segment with inner and outer diameters generally corresponding to those of the existing object. Thus, different portions or segments of the same phantom could then be used as representations of several different existing objects whose size and/or shape differ significantly from each other. For example, the phantom can optionally consist of multiple discrete cylindrical segments of different inner and outer diameters. For another example, the phantom can optionally consist of multiple discrete segments of different sizes and shapes. For another example, the phantom's inner and outer diameters could be constructed to vary gradually. (Optionally calibration marks, of a type which would show clearly in X-ray images, can be embedded within the phantom, in this class of embodiments.)

Where a simulation of the local environment of the existing object is desired, the phantom can be surrounded by materials which substantially simulate the high-energy bulk absorption characteristics of the surroundings of the existing object. For example, where very precise imaging of the bone/soft tissue interface is needed, this embodiment may be particularly advantageous.

The innovative measurement process taught herein uses a high-energy imaging apparatus (such as an X-ray computed tomography device) in combination with a phantom whose solid characteristics generally correspond to the density and shape (preferably including external and internal contours) of the existing object or portion thereof. This combination supports differential error-correction techniques which reduce the magnitude of the imaging errors previously discussed.

In general, the existing structure sought to be measured is first scanned with a high energy scanning device, and measurement data obtained from the scan is recorded. The phantom is then scanned with the same high energy scanning device, with measurement data also being recorded. The known dimensions of the phantom are compared with the measurements obtained from the scan of the phantom. The errors found in the measurement of the phantom provide offset parameters which are used to adjust the scanned data from the existing object.

A further point of invention is a method for construction of a precise physical model with contours matching those of an existing object or portion thereof. This innovative process uses a high-energy imaging apparatus (such as an X-ray computed tomography device) in combination with a phantom whose solid characteristics generally correspond to the density and shape (preferably including external and internal contours) of the existing object or portion thereof. This combination supports differential error-correction techniques which reduce the magnitude of the imaging errors previously discussed.

A further point of invention is a method for prosthesis of bone structures. This innovative process uses a high-energy imaging apparatus (such as an X-ray computed tomography device) in combination with a phantom whose solid characteristics generally correspond to the density and shape (preferably including external and internal contours) of the existing bone structure. Differential error-correction techniques are used to reduce the magnitude of the imaging errors previously discussed. The accurate measurements thus derived for the three-dimensional contours of the existing bone structure are then preferably used to generate a specification for a prosthetic structure which can be fitted to the existing bone structure. This specification is preferably used as a direct input to a manufacturing process (e.g. using numerically controlled machine tools). Thus, a customized prosthesis with a very accurate fit to the existing bone structure is preferably generated before any surgical procedures are started. One advantage of this is that non-cemented prostheses can be used more readily. Another advantage is that prostheses will last longer. Another advantage is that surgical procedures are simplified, since there is less need for mechanical fitting of the prosthesis to the existing bone structure (whether by removal of existing bone, or by modification of the prosthesis, or cementing).

Previous methods for prosthesis have commonly used either two dimensional views (e.g. a combination of anteroposterior and lateral radiographs) or conventional three-dimensional computed tomography information to measure the existing structure, and have required that the actual prosthesis design be done by hand. Therefore, the prosthesis design was based on a limited number of scalar measurements. In the present invention, the design procedures are performed more rapidly and more accurately, using the highly accurate three-dimensional measurements made possible by the innovative methods disclosed herein.

Another advantage of the present invention is that accurate three-dimensional data provided by the innovative methods disclosed herein permit optimal-fit design of prostheses which require intimate bone contact in mechanically important regions. This has been associated with improved non-cemented hip-stem success. The result of these advantages is an optimal-fit design which provides maximum contact of the stem with the bone, while still being insertable. Previous custom design methods produce insertable stems, but fall short of providing maximum contact.

Another innovative teaching disclosed herein is a system which includes both a high-energy imaging apparatus (such as an X-ray computed tomography device) and also one or more phantoms whose solid characteristics generally correspond to the density and shape (preferably including external and internal contours) of the existing object or portion thereof. This system provides measurement accuracy which is significantly improved over conventional computed tomography systems. This combination also enables improved procedures for surgical prosthesis.

The combination of the phantom and scanning apparatus provide an improved system whose capabilities can also be advantageously applied to other imaging problems. However, it is most advantageous in medical applications, for imaging bone structures within a human body.

BRIEF DESCRIPTION OF THE DRAWINGS

The present invention will be described with reference to the accompanying drawings, wherein.

DESCRIPTION OF THE PREFERRED EMBODIMENTS

The numerous innovative teachings of the present application will be described with particular reference to the presently preferred embodiment, wherein these innovative teachings are advantageously applied to the particular problems of orthopedic prosthesis (and, most especially, to hip-stem prostheses). However, it should be understood that this embodiment is only one example of the many advantageous uses of the innovative teachings herein. For example, the various types of innovative phantoms disclosed herein can optionally be constructed to represent any number of existing objects, and are not limited to mammalian bone structures nor to physiological structures generally.

Figure 1:
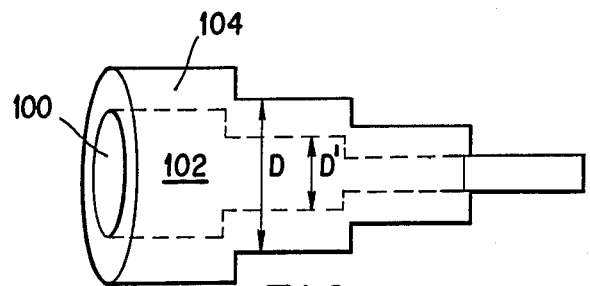
FIG. 1 shows a phantom with a hollow body comprising a single layer of a material. Both the inner and outer diameters of this phantom are of varying lengths.

Referring to FIG. 1, a preferred embodiment of the invention is that of a phantom which is representative of a human femur bone. This phantom has an opening 100 into which a variety of substances can be inserted, and a hollow body 104 consisting of a specified material. The materials used in the construction of the phantom preferably have high-energy absorption characteristics which are substantially similar to those materials which make up the existing structure being measured. Various forms of polymeric materials are suitable.

Figure 6:
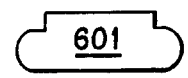
FIG. 6 shows a liquid-tight seal which can be inserted into an opening of the hollow body of a phantom.
Figure 3:
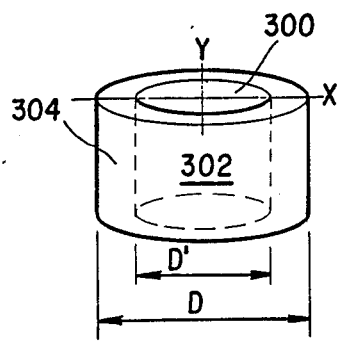
FIG. 3 shows two cross-sectional sections from FIG. 1.
Figure 3:
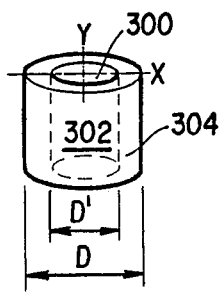

The material of the hollow body 104 has high energy characteristics substantially similar to the cortical bone of a human femur. The hollow portion 102 can be filled through the opening 100 to contain substances with high-energy characteristics substantially similar to those of cancellous bone, fatty tissue, or bone marrow. A liquid-tight seal 601 as shown in FIG. 6 can be fit into opening 100, to prevent any liquids from flowing into or out of the hollow portion 102.

The phantom is preferably cylindrical in shape, having a plurality of abutted cylindrical portions. Diameter D in FIG. 1 represents the outer diameter of an arbitrary cross-sectional slice along the length of the phantom, while diameter D' represents the inner diameter of that cross-sectional slice. Both the outer diameters D and inner diameters D' vary in size throughout the length of the phantom. In one embodiment, the ratios of inner area ($\pi/4$ D'$^2$) to outer area ($\pi/4$ D$^2$) are substantially the same for cross-sections throughout the length of the phantom.

Figure 2:
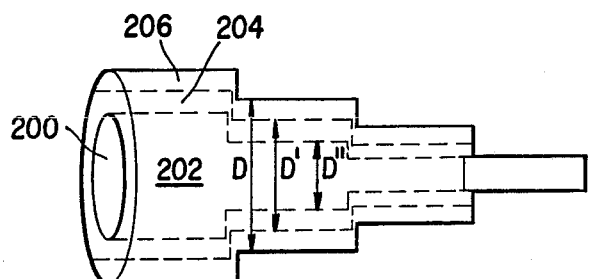
FIG. 2 shows a phantom with a hollow body comprising two layers of differing materials. The inner, outer, and intermediate diameters of this phantom are of varying lengths.

FIG. 2 discloses another embodiment, wherein the hollow body of the phantom contains two layers of materials which differ in high-energy absorption characteristics from one another. Optionally, embodiments containing more than two layers can also be used.

The phantom of FIG. 2 preferably has an outer layer 206 which has high-energy absorption characteristics substantially similar to those of human cortical bone, and an inner layer 204 with high-energy absorption characteristics similar to those of human cancellous bone. The hollow portion 202 of the phantom can be filled through an opening 200 with materials which can have high-energy absorption characteristics similar to fatty tissue, or bone marrow. A liquid-tight seal 601 as shown in FIG. 6 can be fit into opening 200 to prevent any liquids from flowing into or out of the hollow portion 202. The phantom is preferably cylindrical in shape, having a plurality of abutted cylindrical portions. Diameter D in FIG. 2 represents the outer diameter at an arbitrary cross-sectional slice along the length of the phantom, while diameter D'' represents the inner diameter of the same cross-sectional slice. Diameter D' represents the diameter of the cylindrical boundary which separates the two layers of materials in the same region. Diameters D, D', and D'' preferably vary in size throughout the length of the phantom.

Figure 4:
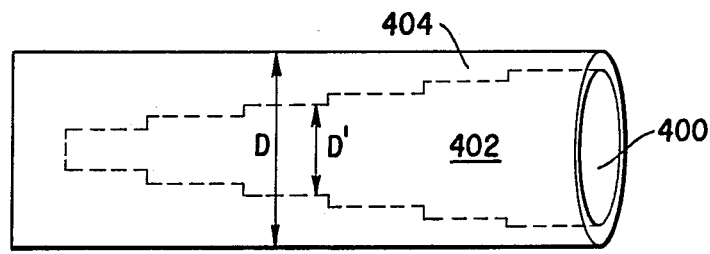
FIG. 4 shows a phantom with a hollow body comprising a single layer of material. The inner diameter takes on several values, while the outer diameter remains constant.

The phantom shown in FIG. 4 has a hollow body 404 of constant diameter D. This hollow body is preferably made of material having high-energy absorption characteristics similar to those of cortical bone. The hollow portion 402 of the phantom can be filled through the opening 400 with materials which can have high-energy absorption characteristics similar to fatty tissue, or bone marrow. A liquid-tight seal 601 as shown in FIG. 6 can be fit into opening 400 to prevent any liquids which may be used from flowing into or out of the hollow portion 402. The phantom is preferably cylindrical in shape, having a plurality of abutted cylindrical portions within the hollow portion 402. Diameter D in FIG. 4 represents the outer diameter at any cross-sectional slice along the length of the phantom, while diameter D' represents the inner diameter at an arbitrary cross-sectional slice. In the embodiment shown, the outer diameter D is of constant length throughout the phantom, while the inner diameters D' vary in size.

Figure 5:
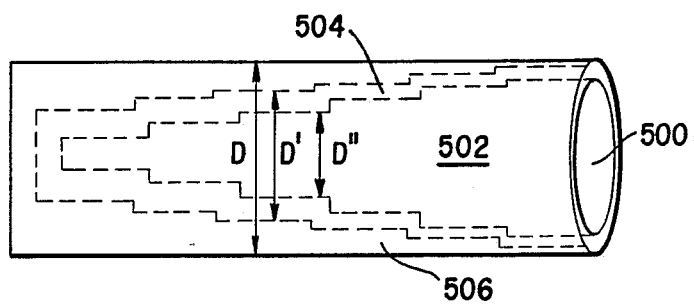
FIG. 5 shows a phantom with a hollow body comprising two layers of differing material. The inner and intermediate diameters take on several values, while the outer diameter remains constant.

The phantom of FIG. 5 contains two layers of materials with differing high-energy absorption characteristics. The outer layer 506 has high-energy absorption characteristics similar to that of human cortical bone, while the inner layer 504 has absorption characteristics similar to that of human cancellous bone. The hollow portion 502 of the phantom can be filled through the opening 500 with materials which can have high-energy absorption characteristics similar to fatty tissue, or bone marrow. A liquid-tight seal 601 as shown in FIG. 6 can be fit into opening 500 to prevent any liquids which may be used from flowing into or out of the hollow portion 502. The phantom is preferably cylindrical in shape, having a plurality of abutted cylindrical portions within the hollow portion 502. Diameter D in FIG. 2 represents the outer diameter at any cross-sectional slice along the length of the phantom, while diameter D'' represents the inner diameter at an arbitrary cross-sectional slice. Diameter D' represents the boundary separating the two layers of materials. Diameters D' and D'' vary in size throughout the length of the phantom, and diameter D (in this embodiment) remains constant.

The phantoms described above are an important innovation in the field of measurement and prosthesis manufacture. Using these phantoms, objects which are difficult to access and measure by conventional means can now be measured with a higher degree of accuracy. One advantage to this is that it allows for the creation of precise physical models of the object or a portion thereof.

The process by which an existing object is measured preferably begins with the manufacture of the phantom or phantoms so that they substantially simulate the high-energy absorption characteristics (assessed at 100 nanometers or less) of the existing object. In addition, the shape of the phantoms should generally correspond to that of the object. The existing object at issue is scanned by a high-energy scanner, such as an X-ray computed tomography device. The scanning device is first used to scan a phantom representative of the existing object. This scanning process can include covering the phantom with material having high-energy absorption properties substantially similar to substances which may surround the existing structure. The errors between the known and scanned measurements of the phantom are then calculated. These errors are incorporated into edge-detection software, which adjusts the scanned data obtained from the existing structure (i.e. the existing bone structure imaged in the body) to compensate for the errors found in the scanning-derived measurements of the existing structure.

One application of this data is to create an accurate three dimensional computer-generated model of the existing structure, which can be used for simulations, for design of prosthetic replacements, or in the practice of various techniques.

If the object is hollow or consists of different layers of materials, the phantom preferably also consists of layers and/or an inner core corresponding to the object in both shape and high-energy absorption characteristics. After the object is scanned with a high-energy device, the phantom is scanned using the same scanning device. Materials simulating the high-energy absorption characteristics and/or shape of a substance surrounding the object can be placed around the phantom during the scan. The measurements obtained from the scan of the phantom are compared with its known dimensions, and any difference in the two measurements is used to adjust the measurement data obtained from the scan of the object.

In one embodiment of the invention where the existing object is a mammalian femur bone, a hollow phantom is preferably constructed using materials which have high-energy absorption characteristics substantially similar to hard cortical and softer cancellous bone material. The hollow portion of the phantom can be filled with material similarly representative of (e.g. having high-energy absorption characteristics substantially similar to) bone marrow.

The cylindrical shape of the phantom generally corresponds to that of a mammalian femur. The phantom consists of several abutted cylindrical segments of progressively increasing inner and outer radii. The increase in size of the internal radius (hollow portion) of the phantom represents the increase in size of the cortical canal. As the inner and outer radius increase, the thickness of the hollow body (i.e. the distance from the hollow portion to the exterior) also increases. The phantoms can be manufactured in different sizes which are representative of a range of differing femur sizes.

In a further optional embodiment, the hollow portion of the phantom can be filled with materials such as titanium or chromium, so that the phantom is to represent a femur containing a hip-stem prosthesis. Bone-cement equivalents can also be used in conjunction with the above-mentioned phantom.

An advantageous process which is enabled by the present invention uses phantoms (preferably of one of the types described) for accurate imaging of a mammalian femur bone, such as that used in X-ray computed tomography. For example, a preferred embodiment uses exposure parameters of 125 kVp (kiloVolts bias applied to the X-ray tube), 230 mAs (milliAmpere-seconds in the X-ray tube), and 3 seconds exposure, using a commercially available Siemens Somatom DR-3 scanner. Two millimeter thick axial scans can be taken every five millimeters (proximal cuts) or at 10 millimeters (distal cuts), starting at the top of the femoral head and proceeding to the midshaft. The data collected from the scan is transferred to an image processor (computer) either directly or via magnetic tape. A preferred image processor is the Gould-/DeAnza IP8500 using a DEC VAX 11/750 as a host.

The next step involves the scanning of the phantom or phantoms under the same high-energy scanning device and same image processor that was used to scan the existing object. In the preferred embodiment, the phantoms of FIG. 1 and FIG. 4 are scanned subsequent to the scanning of the femur. The phantom of FIG. 1 is representative of the upper portion of the femur, while the phantom of FIG. 4 is representative of the lower portion. In this way, the contours of the entire femur can be represented in two smaller, portable pieces. Two calibration passes are then performed with the phantoms to correct the measurements of the physiological structure. That is, the phantom of FIG. 1, which has multiple outside diameters, is preferably used to define data correction factors to accurately estimate the outer profile of the physiological structure, and the phantom of FIG. 4, which has stepped inside diameters, is used to define data corrections to more accurately estimate the internal boundaries of the physiological structure.

The embodiment using two calibration passes solves significant physiological measurement problems. For example, a femur shaft will often have constant outer diameter and changing inner diameter along certain portions of its length, but the femur (like other bones) is likely to flute out at its ends, so that the outer diameter and inner diameter both change. In order to simulate the interface between the bone surface and the soft tissue environment of a human femur bone, the phantoms are placed in a water bath (or enveloped in appropriate equivalent material) during the scanning process.

In another alternative class of embodiments, the phantom can be scanned in the same pass with the patient. When this is done, it is of course necessary to allow for interosseous lucencies between the phantom and the patient. However, if sufficiently accurate estimation can be done with allowance for this introduced interosseous lucency, then this embodiment can provide greater throughput. As with the scanning of the femur, two millimeter thick axial scans can be taken every 5 millimeters (proximal cuts) or 10 millimeters (distal cuts).

After the phantom image data is transferred to the image processor, an edge-detection algorithm provides the basis for outer and inner contours.

The outer (total phantom) and inner (hollow portion) diameters obtained from the scanning device are then compared with the known dimensions of the phantom. The amount of error found to exist between the scanned phantom data and the known dimensions is used in the edge-detection algorithm to adjust for the errors of scanned data of an existing object which, in the preferred embodiment, is a femur bone.

In general, the raw data provided by the imaging scanner in a computed tomography system is quite noisy. Therefore, the image processing algorithms used to regenerate a three-dimensional model must include significant allowances for the noise in the input data.

It is most preferable to have a phantom which is within a millimeter of the dimensions of the existing structure. That is, it is preferable to compute the offset for the actual measurements using data derived from a phantom which is within 5% of the correct raw value. However, a tighter fitting envelope means that more steps must be included on the phantom, and therefore the phantom may need to be a physically larger structure, or else a larger stock of phantoms may be kept on hand. (It should be noted that FIGS. 1 and 2, for clarity, show step sizes much larger than would preferably be used.)

The bone geometry data can also be used purely for computer simulations of surgical procedures. This allows the surgeon to more carefully plan the surgical methods to be used. In addition, the computer simulation can be used for surgical training procedures.

The above-mentioned process can be used to create a physical model of a scanned bone or portion thereof. In a preferred embodiment, the data is used to create an optimal-fit hip stem for insertion into the canal of a mammalian femur bone. This stem is preferably made of titanium, but can also be made of rigid plastic.

The software procedures used in the best mode as presently contemplated will now be described in considerable detail. However, it should be recognized that the numerous specific details given are merely illustrative, and do not necessarily delimit features of the invention.

Using the bone geometry data, a stem-canal fit and fill analysis program can be used in a preferred embodiment to automatically quantify stem-inner cortical bone contact (fit) and stem filling of the canal. Fit is determined by calculating the distance between the stem and inner cortical surface along lines perpendicular to the stem contour. Fill is determined by calculating the areas inside the closed stem and inner bone contours.

The fit and fill analysis program consists of three interactive software modules. The preprocessing module simulates the surgical bone preparation and prepares the computer tomography generated bone model for stem insertion. First, a simulation of the resection of the femoral head and neck is done, and bone is removed in the femoral canal area by reaming and rasping to prepare for insertion of the hip stem.

The computer operator (either a technician or a surgeon) simulates exposure of the canal. The level and angle of the neck cut and greater trochanter cut are specified on an anterior-posterior model view of the femur using (in this embodiment) the bone geometry data. The desired stem length is also input at this time. The surgical cuts are simulated on the bone model by the removal of the involved surface polygons. The program then presents the modified data and asks for verification. If approved, the operator proceeds with the next step of this module. If disapproved, the data is reinitialized and the process repeated.

An exact-fitting implant would completely fill the entire femoral canal. Such an implant is, however, impossible to insert, due to the complex shape of the medullary canal. Some areas on the implant must be removed to allow insertion into the femur. Areas needed to optimize stem-bone load transfer and to minimize stem motion must thus be identified.

Optimal load transfer to axial forces and bending moments is achieved by giving a high priority to maintaining an exact fit along the proximal medial wall of the femur. Stem filling of the proximal canal also has high priority because it helps to achieve axial torsional stability for the stem. Additionally, the stem should not wedge distally within the canal. However, contact at the distal lateral tip of the stem must be maintained to prevent medial-lateral rocking.

With these criteria, priority scores are automatically applied to the canal model by the software. The scoring routine initially uses a set of circular templates (one for each axial canal section), each divided into at least 40 equally spaced radial sectors. Each sector has an assigned score. The data points of each canal section are assigned the score of the sector which has been applied over that data point. The canal scores can also be modified interactively as desired.

Point editing of the models can also be performed in this preprocessing module. This interactive process permits the complete redefinition of the prepared three-dimensional canal data. Editing is performed on one axial contour at a time. Options include moving, adding, deleting, or rescoring any contour point. The canal and outer cortical contours are displayed in an upper screen window; the section being edited is magnified and displayed in a lower screen window. The outer cortical contours are included to provide a realistic boundary cue during the reaming and rasping of the canal model. Three-dimensional wireframe views may be intermittently displayed to check the modifications made during point editing.

For the stem to fit as designed, the surgeon must be able to prepare the actual bone in a manner similar to the computer simulation. To achieve this, the software references bony landmarks available to the surgeon at the time of operation.

Once the computer simulation of the canal has been prepared, the data obtained from the pre-processing module is submitted to the stem design module. The initial stem model is set equal to the prepared canal, ensuring that the stem starts out completely filling the canal. The priority scores assigned to the computer model of the femur are transposed onto the adjacent areas of the stem model. Thus, areas of the stem which are adjacent to high priority areas of the femur are themselves given a high priority.

Design begins by translating the stem (within this computer model simulation) an incremental amount up the vertical axis of the canal. (By repetition of this and the following steps, the stem will eventually be removed entirely from the canal.)

Incremental rotations on three orthogonal axes around the contact point are performed. At a given orientation, a stem-canal surface overlap score is determined by summing over all the stem points the distance from the point to the canal polygon surface, measured along the vector to the stem section's centroid. The result is then weighted by the point's priority score. Minimization of the overlap score is obtained by applying a modification of Newton's optimization algorithm successively to each axis of rotation. At the orientation for minimum score, the overlapping stem points are moved along the previously mentioned directional vector to the canal polygon and redefined at that intersection. Thus, for that particular vertical level, the stem model is once again completely within the canal.

The stem is then elevated to the next level, and the process is repeated until the entire stem has passed through the proximal femoral neck cut. The resultant stem shape describes the optimal stem-bone fit that is still insertable.

The postprocessing module allows the operator to verify the stem design by viewing the stem-bone computer model in either two or three dimensions. A cutting algorithm sections and displays the stem-bone model at any level in any plane. The point editor is available for making minor modifications to the stem.

The bone and stem model data is used as input to a computer graphics modeling package, MOVIE.BYU (developed at Brigham Young University), and the Ansys finite element analysis package. Computer graphic methods are used for visualization and for qualitative assessments of stem-bone fit.

In summary, this design software produces bone and stem model data. The data can be input into a computerized numerically controlled (CNC) machine to produce actual-size plastic bone models and/or optimal-fit metal implants. The plastic bone models have been used in surgical rehearsals of difficult osteotomy and reconstruction procedures. Metallic custom stems have been produced for joint replacement.

The above mentioned description of a stem design program was published in an article co-authored by John Granholm, Douglas Robertson, Peter Walker, and Philip Nelson. The publishing periodical was the IEEE CG&A, February 1987, and is incorporated in its entirety by reference thereto.

A system for the creation of protheses such as the artificial hip-stem can be implemented using the previously mentioned devices. Such a system will consist of a phantom or phantoms which simulate an existing structure such as an mammalian femur bone, a high-energy scanner such as a computer tomography X-ray device, and a computer for outputting accurate bone geometry data.

It should be noted that the advantages of a three-dimensionally contoured phantom for simulating physiological structures could also be applied to NMR (nuclear magnetic resonance) techniques for measuring physical structures. However, these techniques are substantially more advantageous in the context of high-energy imaging, and most especially in the area of high-energy imaging of bone structures.

A preferred embodiment of a computed tomography X-ray device for the above mentioned system consists of one or more X-ray sources in which the beam is deflected by electromagnetic means, or where the mechanical movement of one or more sources of X-rays are kept to a minimum. This type of X-ray computer tomography device is generally known as a fourth-generation machine. Scanners of this type can achieve scan times of 33 milliseconds and repetition rates of 24 scans a second. The speeds make it possible to effectively image a fast-moving object, such as a beating heart.

Additional features of the phantoms and processes or systems which utilize them are described in a pending publication co-authored by Douglas Robertson, Peter Walker, John Granholm, Philip Nelson, Peter Weiss, Elliot Fishman, and Donna Magid, entitled "The Design of Custom Hip Stem Prosthesis Using Three-Dimensional CT Modeling." This article is scheduled for publication on Sept. 15, 1987 in the Journal of Computer Assisted Tomography, and is incorporated herein in its entirety by reference thereto.

The preferred embodiment of the system provided by the present invention uses multiple sets of phantoms in a computed tomography lab. Thus, for example, one set has diameters and densities suitable for estimation of leg bones, one set suitable for arm bone dimensions and densities, one set for hands, one set for feet, one set for spine, and one set for skull.

It should be noted that (as is well known to those skilled in the art of radiology) the "equivalent absorption characteristics" referred to above are preferably selected for equivalency under generally predetermined imaging conditions. That is, the materials used in the phantom are most preferably selected for equivalency at the X-ray energies which are expected to be used. For example, if the X-ray tube used in the scanning device were operated at 15 kilovolts instead of 125, or possibly even if a tube having a different type of X-ray target were used, it might be necessary to manufacture the phantom using different materials to attain equivalent high-energy absorption characteristics of the scanned object. However, the selection of equivalent absorption materials is well understood by those skilled in the art.

As will be recognized by those skilled in the art, the innovative concepts described in the present application can be modified and varied over a tremendous range of applications, and accordingly their scope is not limited except by the allowed claims.

What I claim is:

1. A phantom for simulating an existing structure, comprising:
a hollow body of a solid material, wherein internal and external surfaces of said hollow body comprises a plurality of cylindrical sections of multiple distinct radii in substantially abutting end-to-end relationship; said material having high-energy absorption characteristics substantially similar to those of the existing structure.

2. The phantom of claim 1, wherein said high-energy absorption characteristics are assessed at wavelengths of 100 nanometers or less.

3. The phantom of claim 2, wherein the existing structure has a cavity therein, which is filled or partly filled with a substance,
wherein said phantom comprises a hollow portion of said hollow body which is filled (wholly or partly) filled with a material having high-energy absorption characteristics substantially similar to that of the substance within the cavity of said existing structure.

4. The phantom of claim 2, wherein the existing structure is partly or completely enveloped by a lower-density substance,
wherein the external surface of said phantom is at least partly enveloped by a material whose high-energy absorption characteristics are substantially similar to that of the substance enveloping the existing structure.

5. The phantom of claim 1, wherein the thickness of said hollow body between the external and internal surfaces of said phantom varies in substantial correspondence with thickness variations of the existing structure.

6. The phantom of claim 1, wherein the existing structure consists of a plurality of layers of material with defined boundaries between said layers, wherein said phantom contains corresponding materials which form a plurality of layers whose boundaries generally correspond to those of corresponding layers in the existing structure, wherein said materials of said layers have high-energy absorption characteristics substantially similar to those of material in corresponding layers of the existing structure.

7. The phantom of claim 1, wherein said external surface of said phantom has multiple diameters generally spanning a full range of values within which external diameters of the existing structure are expected to fall.

8. The phantom of claim 1, wherein said internal surface of said phantom has multiple diameters generally spanning a full range of values within which internal diameters of the existing structure are expected to fall.

9. The phantom of claim 1, wherein the thickness of said hollow body between the external and internal surfaces of said phantom varies in correspondence with thickness variations of the existing structure.

10. The phantom of claim 1, wherein the existing structure is partly or completely enveloped by a substance, wherein the external surface of said phantom is similarly enveloped by a material whose high-energy absorption characteristics are substantially similar to that of the substance enveloping the existing structure.

11. A method for creating a physical model with at least some contours corresponding to those of an anatomical structure (or portion thereof) within a living organism, comprising the steps of:
(a) providing a phantom which generally corresponds to the shape of the existing structure in vivo, wherein various parts of said phantom have high-energy absorption characteristics corresponding to those of respective parts of the existing structure;
(b) scanning the existing structure with a high-energy scanning device to derive three-dimensional data corresponding to the three-dimensional structure of the existing object;
(c) scanning said phantom with said high-energy scanning device to derive three-dimensional data corresponding to the three-dimensional structure of said phantom;
(d) modifying the three-dimensional data obtained from step (b), in accordance with differences between the dimensions obtained from step (c) and the actual physical dimensions of said phantom, to provide more accurate three-dimensional data corresponding to the three-dimensional structure of the existing object; and
(e) fabricating a physical model with at least some contours defined by said modified three-dimensional data provided by said step (d).

12. The method of claim 11, wherein edge-detection algorithms are used to help define said three-dimensional data in said steps (b) and (c).

13. A method for prosthesis of bone structures, comprising the steps of:

(a) providing a phantom which generally corresponds to the shape of the existing structure in vivo, wherein various parts of said phantom have high-energy absorption characteristics corresponding to those of respective parts of the existing structure;

(b) scanning the existing structure with a high-energy scanning device to derive three-dimensional data corresponding to the three-dimensional structure of the existing object;

(c) scanning said phantom with said high-energy scanning device to derive three-dimensional data corresponding to the three-dimensional structure of said phantom;

(d) modifying the three-dimensional data obtained from step (b), in accordance with differences between the dimensions obtained from step (c) and the actual physical dimensions of said phantom, to provide more accurate three-dimensional data corresponding to the three-dimensional structure of the existing object;

(e) providing a specific prosthetic structure with at least some contours complementary to the modified three-dimensional data provided by said step (d); and (f) surgically implanting said prosthetic structure in the patient.

14. The method of claim 13, wherein said prosthetic structure is provided by numerically-controlled fabrication, using the modified three-dimensional data provided by said step (d) to define a specification.

* * * * *